United States Patent [19]
Steinmetz

[11] Patent Number: 5,847,807
[45] Date of Patent: Dec. 8, 1998

[54] ARRANGEMENT FOR TILTABLY JOURNALLING AN OPHTHALMOLOGIC TREATMENT AND/OR EXAMINING APPARATUS

[75] Inventor: Dietmar Steinmetz, Jena, Germany

[73] Assignee: Carl Zeiss Jena GmbH, Jena, Germany

[21] Appl. No.: 838,190

[22] Filed: Apr. 16, 1997

[30] Foreign Application Priority Data

Apr. 16, 1996 [DE] Germany .......................... 196 14 749.2

[51] Int. Cl.⁶ ................................................ A61B 3/02
[52] U.S. Cl. ............................................................ 351/245
[58] Field of Search .............................................. 351/245

[56] References Cited

U.S. PATENT DOCUMENTS

| | | | |
|---|---|---|---|
| 2,062,029 | 11/1936 | Hunt | 351/245 |
| 5,000,563 | 3/1991 | Gisel et al. | 351/245 |

FOREIGN PATENT DOCUMENTS

| | | | |
|---|---|---|---|
| 1189759 | 3/1965 | Germany . | |
| 1192423 | 3/1965 | Germany | 351/245 |
| 1231030 | 12/1966 | Germany . | |
| 2659444 | 1/1978 | Germany . | |
| 8034259 | 5/1981 | Germany . | |
| 4111754 | 10/1992 | Germany . | |

OTHER PUBLICATIONS

"OPTON Fundus Fotografie macht einen Fall zum klaren Fall".
"Fundus camera FK 30".

*Primary Examiner*—Huy Mai
*Attorney, Agent, or Firm*—Walter Ottesen

[57] ABSTRACT

The invention is directed to an arrangement for tiltably journalling an ophthalmologic treatment and/or examining apparatus. The arrangement includes a mount and an arcuate guide fixedly attached at an end thereof to the mount. Guide elements are mounted on the apparatus for movably guiding the apparatus along the arcuate guide to tilt the apparatus to a desired position. A pressure-spring device has a first end pivotally connected to the apparatus and a second end pivotally connected to the mount whereby the weight of the apparatus is compensated as the apparatus is tilted when moved along the arcuate guide. The arrangement further includes a mechanism for blocking and deblocking the spring action of the pressure-spring device. A lever assembly imparts a tilting movement to the apparatus. The lever assembly has a first pivot connection whereat the Lever assembly is connected to the mount and a second pivot connection whereat the lever assembly is connected to the apparatus.

16 Claims, 2 Drawing Sheets

ARRANGEMENT FOR TILTABLY JOURNALLING AN OPHTHALMOLOGIC TREATMENT AND/OR EXAMINING APPARATUS

FIELD OF THE INVENTION

The invention relates to an arrangement for tiltably journalling an ophthalmologic treatment and/or examining apparatus which incorporates an arcuate guide for the apparatus. The apparatus is, for example, a retina camera pivotable about a horizontal axis.

Background of the Invention

An arcuate guide for a fundus camera is shown in the brochures entitled "OPTON Fundus Fotografie", publication number F 30-245-d and "Fundus camera FK 30", publication number FT 30-172-e both published by Opton Feintechnik GmbH of Oberkochen, Germany.

The fundus camera glides on an arcuate guide via guide rollers. A transmission having a hand wheel engages the arcuate guide. The adjustment of the position of the apparatus takes place via the hand wheel and the transmission. An upgearing as high as possible and a self-holding transmission must be provided in order to prevent the apparatus from becoming dislodged from the arcuate guide. This is relatively complex and tedious. A rapid adjusting movement over longer pivot paths is not possible.

SUMMARY OF THE INVENTION

It is an object of the invention to provide an arrangement for tiltably journalling an ophthalmologic treatment and/or examining apparatus which avoids the above-mentioned disadvantages.

The arrangement of the invention is for tiltably journalling an ophthalmologic treatment and/or examining apparatus. The arrangement includes: a mount; an arcuate guide having an end portion; means for fixedly attaching the arcuate guide to the mount; a plurality of guide elements mounted on the apparatus for movably guiding the apparatus along the arcuate guide to tilt the apparatus to a desired position; and, a pressure-spring device having a first end pivotally connected to the apparatus and having a second end pivotally connected to the mount whereby the weight of the apparatus is compensated as the apparatus is tilted when moved along the arcuate guide.

An adjustment without actuating the transmission is also possible directly on the apparatus because the hand wheel transmission no longer requires any self-holding. In this way, the transmission assembly is significantly simplified.

A hand wheel transmission can be completely eliminated by utilizing the blockable shock absorber shown in FIG. 2. A longer lever arm ensures a more convenient adjustment.

An adjustable compensation of weight is achieved with an adjustable and latchable change of the connecting point of the spring compensator on the apparatus or on the bearing.

BRIEF DESCRIPTION OF THE DRAWINGS

The invention will now be described with reference o the drawings wherein:

FIG. 1a is a detail section view of the hand-wheel transmission taken along line A—A of FIG. 1; and, FIG. 2 is a schematic of a second embodiment of the arrangement according to the invention.

DESCRIPTION OF THE PREFERRED EMBODIMENTS OF THE INVENTION

Figure 1:
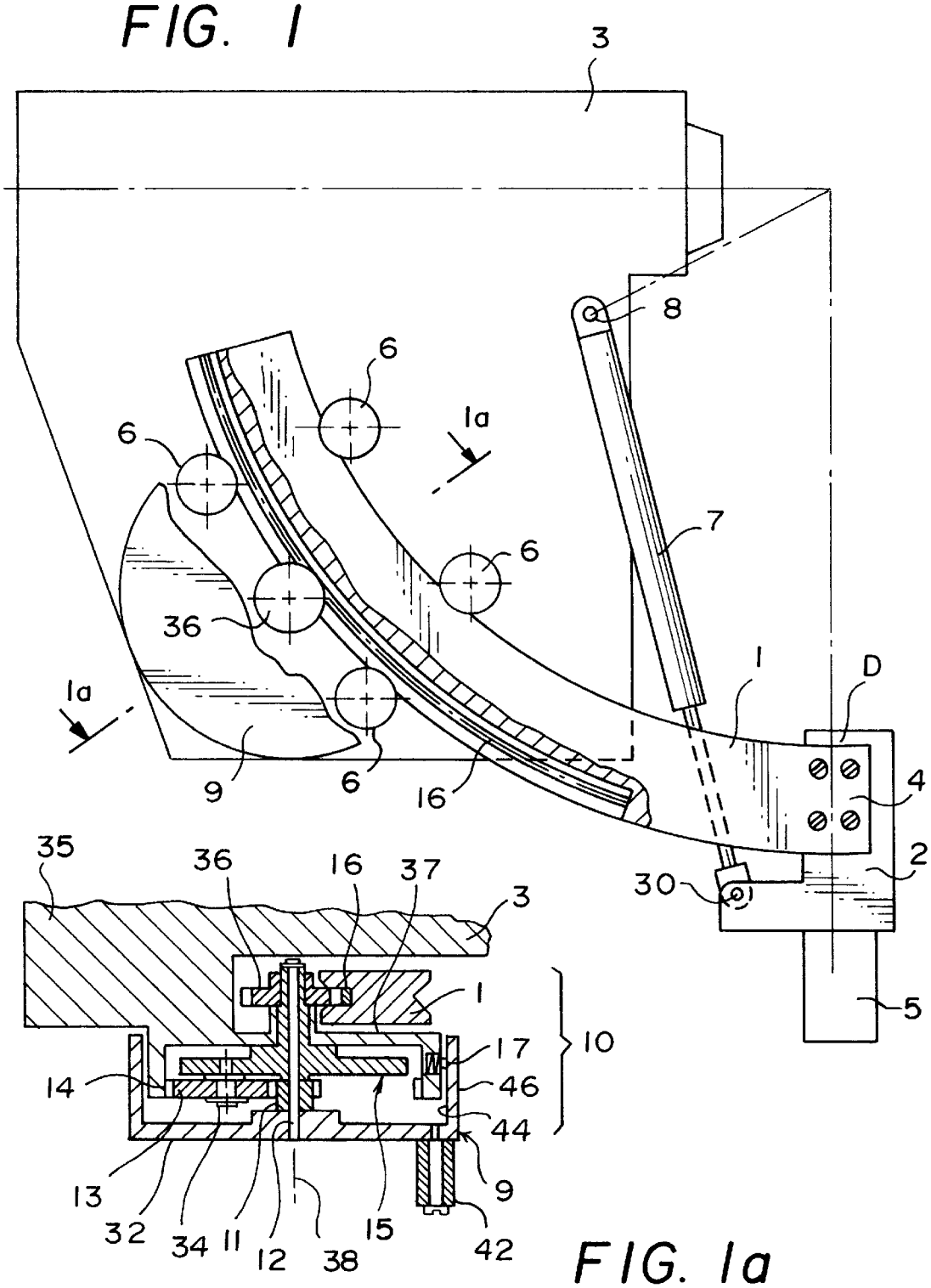
FIG. 1 is a first embodiment of the arrangement of the invention for tiltably journalling an ophthalmologic treatment and/or examining apparatus.

An arcuate guide 1 is attached to a pivot bearing 2 at a location 4 for rotating an examining apparatus 3 about a rotational axis D. The apparatus 3 is only shown in outline.

The pivot bearing 2 is shown mounted on a bolt 5 which, in turn, is fixedly mounted in a table (not shown).

Four rollers 6 are mounted on the apparatus 3 and guide the apparatus on the arcuate guide 1. The apparatus 3 is braced via a shock absorber 7 on the pivot bearing 2 for compensating for the weight of the apparatus 3. The shock absorber 7 is configured as a gas-pressure shock absorber.

The attachment points of the shock absorber 7 on the apparatus 3 at point 8 as well as on the pivot bearing 2 at point 30 are dependent upon the weight which must be compensated. Usually, these attachment points are fixed for an averages weight so that the lowest possible residual force is required to move the apparatus 3 along the arcuate guide 1.

However, it can be advantageous to make one or both attachment points variably adjustable, for example, on a latchable linear or arcuately shaped guide (not shown) so that an additional adjustment to the particular apparatus weight is provided.

A coarse adjustment of the apparatus 3 along the arcuate guide 1 via the rollers 6 is in essence possible manually because of the achieved weight compensation.

The fine drive of the apparatus 3 is achieved via an integrated planetary transmission 10 which includes hand wheel 9 having a disc 32 and a handle 42. The planetary transmission 10 is rotatably journalled in the apparatus 3. A pinion 11 mounted on a shaft 12 rotates when the hand wheel 9 is rotated. By rotating the hand wheel 9 at handle 42 to rotate about axis 38, a planetary wheel 13 is caused to roll along an internal gear 14 fixed to the housing 35 of the apparatus 3. The planetary wheel 13 is driven by the hand wheel 9 via the pinion 11 which engages the planetary wheel 13.

The gear wheel assembly 15 includes a gear wheel 35 which is fixedly attached to element 37 of the gear assembly 15. A pin coupling 34 connects planetary wheel 13 to element 37 of the gear assembly 15 so that the latter is entrained for rotational movement about longitudinal axis 38 as the planetary wheel 13 rolls over and along the internal gear 14. The shaft 12 is fixedly connected to the disc 32 and the pinion 11 but is freely rotatably within the gear assembly 15. The gear wheel 36 meshes with arcuate gear 16 on arcuate guide 1 so that the apparatus 3 can be finely displaced along the arcuate guide 1 thereby also tilting the apparatus 3.

A spring biased bolt 17 includes a spring which presses the bolt 17 against the inner wall surface 44 of annular wall 46 of hand wheel 9. The force with which bolt 17 is applied to wall surface 44 is however not excessive so that a rapid manual coarse adjustment of the apparatus 3 along arcuate guide 1 is nonetheless possible.

Figure 2:
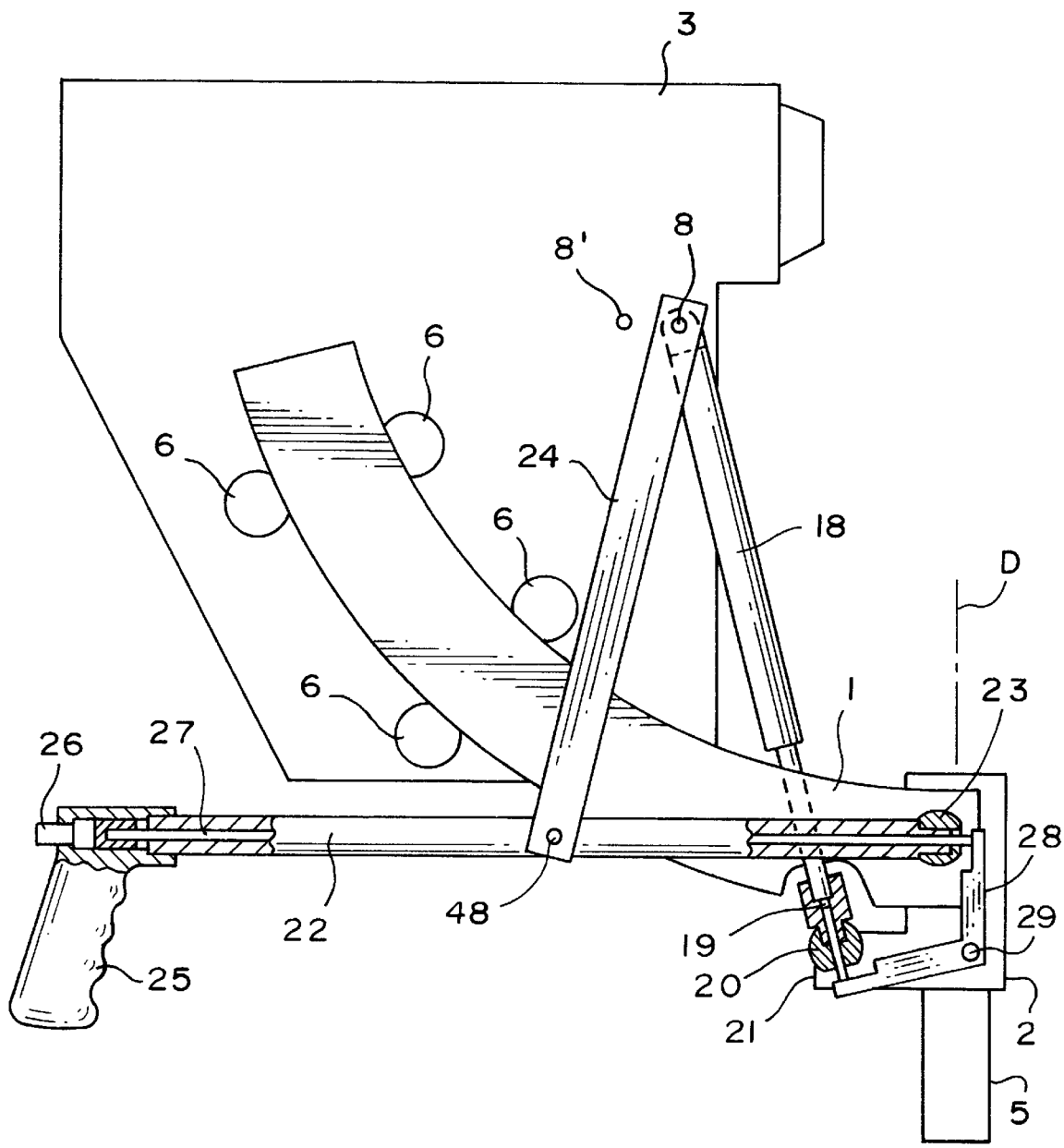

In the embodiment of FIG. 2, a blockable gas spring 18 is provided in lieu of the shock absorber. Blocking is released by actuating a valve 19 of the gas spring 18. The gas spring 18 is journalled in a bearing 20 in which a pin 21 is slideably guided for operating on the blocking valve 19. The bearing 20 is attached to the pivot bearing 2, which, in turn, is mounted on bolt 5 so as to be rotatable thereon.

An additional lever 22 is journalled in a bearing 23 which is also attached to the pivot bearing 2. The bearing 23 functions as a guide for a rod 27 movably mounted in lever 22. The lever 22 is connected via rod 24 to the connecting point 8 of the gas spring 18 on the apparatus 3. The rod 24 is connected to lever 22 at connecting point 48 and can be connected to the apparatus 3 at a point other than point 8 if desired. For example, the rod 24 can be connected to the apparatus 3 at point 8'.

The lever 22 is provided with a handle 25 in which a pressure piece 26 is guided. A bell-crank lever 28 is pivotally mounted on pivot bearing 2. When the pressure piece 26 is actuated with the thumb by an operator, the rod 27, which is connected to the pressure piece 26 and guided in bearing 23, acts on the bell-crank lever 28 and pivots the same about pivot point 29 and actuates the valve 19 of the gas spring via the pin 21 so that the blocking action of the gas spring 18 is released.

A movement of the handle 25 effects a change in the inclination or tilt of the apparatus 3 via the rod 24 or even a rotation of apparatus 3 in the pivot bearing 2 about the vertical rotational axis D. The change of inclination of the apparatus 3 is facilitated because of the long lever arm 22 and because of the weight compensation. When the correct adjusting point is found, the pressure piece 26 is released by removing the thumb therefrom and the apparatus 3 is fixed in this position by the blocked gas spring 18.

It is understood that the foregoing description is that of the preferred embodiments of the invention and that various changes and modifications may be made thereto without departing from the spirit and scope of the invention as defined in the appended claims.

What is claimed is:

1. An arrangement for tiltably journalling an ophthalmologic treatment and/or examining apparatus, the arrangement comprising:

a mount;

an arcuate guide having an end portion;

means for fixedly attaching said arcuate guide to said mount;

a plurality of guide elements mounted on said apparatus for movably guiding said apparatus along said arcuate guide to tilt said apparatus to a desired position; and, a pressure-spring device having a first end pivotally connected to said apparatus and having a second end pivotally connected to said mount whereby the weight of said apparatus is compensated as said apparatus is tilted when moved along said arcuate guide.

2. The arrangement of claim 1, said plurality of guide elements being a plurality of rollers in rolling contact engagement with said arcuate guide.

3. The arrangement of claim 2, said pressure-spring device being an elongated device crossing over said arcuate guide.

4. The arrangement of claim 3, said pressure-spring device being a gas-pressure spring.

5. The arrangement of claim 3, wherein said first end of said pressure-spring device is pivotally connected to said apparatus at a fixed location thereon.

6. The arrangement of claim 3, further comprising means for adjusting the location at which said first end of said pressure spring is pivotally connected to said apparatus whereby the compensation of said weight by said pressure-spring device is adjusted.

7. The arrangement of claim 1, further comprising an actuating device mounted on said apparatus and being operatively connected to said arcuate guide for tilting said apparatus.

8. The arrangement of claim 7, said actuating device including: a gear on said arcuate guide; a hand wheel; a transmission connecting said hand wheel to said gear; and, said transmission being adapted to permit a fine adjustment of the tilt position of said apparatus by adjusting said hand wheel.

9. The arrangement of claim 8, said transmission being c nonself-holding transmission.

10. The arrangement of claim 9, said transmission being a planetary transmission.

11. The arrangement of claim 1, a pivot bearing for pivotally journalling said mount for rotation about a vertical axis thereby permitting said arcuate guide and said apparatus to be pivoted about said axis.

12. The arrangement of claim 1, further comprising means for blocking and deblocking the spring action of said pressure-spring device.

13. The arrangement of claim 12, further comprising a lever assembly for imparting a tilting movement to said apparatus; said lever assembly having a first pivot connection whereat said lever assembly is connected to said mount and a second pivot connection whereat said lever assembly is connected to said apparatus.

14. The arrangement of claim 13, said lever assembly including a handle and a lever arm to which said first and second pivot connections are connected; and, said lever arm being movable via said handle to effect a tilting of said apparatus via said second pivot connection.

15. The arrangement of claim 14, said blocking and deblocking means including a valve in said pressure-spring device; and, an actuator mechanism integrated in said handle and lever arm for operating on said valve to block and deblock said pressure-spring device.

16. The arrangement of claim 15, said actuator mechanism further including a lever pivotally connected to said mount for interfacing between said valve and said actuator mechanism.

* * * * *

UNITED STATES PATENT AND TRADEMARK OFFICE
CERTIFICATE OF CORRECTION

PATENT NO. : 5,847,807
DATED : December 8, 1998
INVENTOR(S) : Dietmar Steinmetz

It is certified that error appears in the above-identified patent and that said Letters Patent is hereby corrected as shown below:

On the title page, in the Abstract, line 15: delete "Lever" and substitute -- lever -- therefor.

In column 2, line 21: delete "averages" and substitute -- average -- therefor.

In column 2, line 43: delete "35" and substitute -- 36 -- therefor.

In column 4, line 22: delete "c" and substitute -- a -- therefor.

Signed and Sealed this

Eighteenth Day of May, 1999

Attest:

Attesting Officer

Q. TODD DICKINSON

Acting Commissioner of Patents and Trademarks